United States Patent
Brunson (10) Patent No.: US 11,950,623 B2
(45) Date of Patent: *Apr. 9, 2024

(54) PLANT PRODUCT INFUSED WITH OIL AND METHOD OF INFUSION

(71) Applicant: BIG 5 PROPERTIES INC., Henderson, NV (US)

(72) Inventor: Michael A. Brunson, Carlsbad, CA (US)

(73) Assignee: BIG 5 PROPERTIES INC.

( * ) Notice: Subject to any disclaimer, the term of this patent is extended or adjusted under 35 U.S.C. 154(b) by 174 days.

This patent is subject to a terminal disclaimer.

(21) Appl. No.: 17/135,549

(22) Filed: Dec. 28, 2020

(65) Prior Publication Data

US 2021/0137156 A1 May 13, 2021

Related U.S. Application Data (63) Continuation-in-part of application No. 16/819,082, filed on Mar. 14, 2020, now Pat. No. 10,874,703, which is a continuation-in-part of application No. PCT/US2018/051238, filed on Sep. 14, 2018.

(60) Provisional application No. 62/559,255, filed on Sep. 15, 2017.

(30) Foreign Application Priority Data

Apr. 2, 2020 (AU) .................................. 2018347858
Apr. 14, 2020 (AU) ................................ 2020202488

(51) Int. Cl.
| | |
|---|---|
| *A61K 36/00* | (2006.01) |
| *A24B 15/24* | (2006.01) |
| *A24B 15/30* | (2006.01) |
| *A61K 31/05* | (2006.01) |
| *A61K 36/185* | (2006.01) |
| *A24B 15/26* | (2006.01) |

(52) U.S. Cl.
CPC .......... *A24B 15/241* (2013.01); *A24B 15/303* (2013.01); *A61K 31/05* (2013.01); *A61K 36/185* (2013.01); *A24B 15/26* (2013.01); *A61K 2236/37* (2013.01)

(58) Field of Classification Search
None
See application file for complete search history.

(56) References Cited

U.S. PATENT DOCUMENTS

| | | | |
|---|---|---|---|
| 7,048,941 B2 | 5/2006 | Altafer et al. | |
| 8,469,038 B2 | 6/2013 | Sinclair, Jr. | |
| 9,035,130 B2 | 5/2015 | De Meijer | |
| 9,186,386 B2 | 11/2015 | Speier | |
| 9,474,725 B1 | 10/2016 | Reillo et al. | |
| 9,532,593 B2 | 1/2017 | Turner | |
| 9,539,216 B2 | 1/2017 | Miller | |
| 10,369,178 B2 | 8/2019 | Greenbaum et al. | |
| 2012/0124704 A1 | 5/2012 | Szymanowski | |
| 2016/0243177 A1 | 8/2016 | Franklin et al. | |
| 2016/0296464 A1* | 10/2016 | Lindsay | B65B 11/48 |
| 2016/0324776 A1 | 11/2016 | Glatzel | |
| 2016/0367479 A1* | 12/2016 | Reillo | A61P 13/08 |
| 2017/0112187 A1 | 4/2017 | Ostrander | |
| 2017/0112188 A1 | 4/2017 | Ostrander | |
| 2017/0136076 A1 | 5/2017 | Soman et al. | |

FOREIGN PATENT DOCUMENTS

| | | |
|---|---|---|
| CN | 101214085 | 7/2008 |
| CN | 102613694 | 8/2012 |
| CN | 103351950 | 10/2013 |
| JP | 2017522901 | 8/2017 |
| KR | 20100060749 | 6/2010 |
| WO | 2011095621 | 8/2011 |
| WO | 2016169815 | 10/2016 |
| WO | 2016187156 | 11/2016 |
| WO | 2016187156 A1 | 11/2016 |
| WO | WO-2016187156 A1 * | 11/2016 ........ A61M 15/0025 |

OTHER PUBLICATIONS (Forums) "THC coated rolling papers" Aug. 20, 2016; (retrieved Mar. 22, 2019). Retrieved from the Internet: http://boards.cannabis.com/threads/thc-coated-rolling-papers.114509.
(Forums) "THC coated rolling papers" Aug. 30, 2016; [retrieved Mar. 22, 2019] . Retrieved 1-15from the Internet.
International Search Report and Written Opinion dated Jun. 10, 2019 for corresponding International Application No. PCT/US2018/51238.

* cited by examiner

*Primary Examiner* — Russell G Fiebig
(74) *Attorney, Agent, or Firm* — Allison M. Corder (57) ABSTRACT

An oil-infused plant product and method of infusing is provided. The method includes placing dried botanical matter with an alcohol and oil mixture into a pressurizable container, pressurizing and heating the pressurizable container, allowing the botanical matter and oil/alcohol mixture to remain in the container for a development time period while the oil is drawn into the botanical matter, and removing the oil/alcohol mixture via a vacuum. The botanical matter may be a processed plant matter, such as a blunt wrapper, or may be a natural or minimally processed plant matter, such as dried edible plants, smokable herbs, or herbs suitable for brewing (such as tea, coffee, and herbal tea components). The oil may be any nontoxic oil.

13 Claims, 3 Drawing Sheets

PLANT PRODUCT INFUSED WITH OIL AND METHOD OF INFUSION

CROSS REFERENCE TO RELATED APPLICATIONS

The present application is a continuation-in-part of co-pending U.S. patent application Ser. No. 16/819,082 filed on Mar. 14, 2020 (now U.S. Pat. No. 10,874,703), which is a bypass continuation-in-part application of PCT International Application No. PCT/US18/51238 having an international filing date of Sep. 14, 2018 and designating the United States, the PCT International Application claiming a priority date of Sep. 15, 2017 based upon prior-filed U.S. Provisional Patent Application No. 62/559,255; and the present application claims priority to Australia Patent Application No. AU2020202488 filed on Apr. 14, 2020, which is a division of Australia Patent Application No. AU2018347858 filed on Apr. 2, 2020, which claims priority to PCT International Application No. PCT/US18/51238 having an international filing date of Sep. 14, 2018; the entire contents of the aforesaid applications being incorporated herein by reference.

FIELD OF INVENTION

This invention relates generally to plant materials, and, more particularly, to a plant product that is infused with oil and to a method of infusion of this plant matter.

BACKGROUND OF THE INVENTION

Over the ages, people have used numerous plants for improving health and for medicinal purposes. Recently there has been a growing interest in this traditional knowledge and in developing new therapeutic uses for plant matter. Often applying oil onto plant matter is desired, such as to complement the medicinal benefits or the integrity or functionality of the end product. But problems have arisen in trying to add oil to dry plant matter, because the oil is not absorbed but remains deposited on the outside. As the oil is not evenly distributed, the proportion of oil to plant matter is not consistent.

Since the oil and plant matter is to be used medicinally, a practitioner needs to prescribe a particular dosage. But this has not been an achievable goal due to the inconsistency of the oil and plant matter combination product, the inability to control the potency or ratio of the oil to plant matter, and the incapability of increasing the percentage of oil in the plant matter.

Various plants and various oils may be used therapeutically, and each provide different chemical compositions that may be used to address different indications or needs. For example, one combination currently of interest to people is the combination of plant matter with *Cannabis* oil, because the health benefits of cannabinoids from plants of the genus *Cannabis* have recently been recognized. At least 113 of these phytocannabinoids (exhibiting varying effects) have been isolated from plants of the *Cannabis* genus. Of these, the primary psychoactive compound is delta-9 tetrahydrocannabinol, commonly known as THC. Another major phytocannabinoid is cannabidiol, commonly abbreviated as CBD, which accounts for up to 40% of the extract from some cultivated varieties of the *Cannabis* genus. There is a wide range of THC and CBD potency between *Cannabis* plant varieties.

CBD is not psychoactive, but instead it has an anti-psychotic effect that may lessen anxiety. A report, *A Primer about Cannabidiol and the Benefits of CBD*, published in Huffington Post on Mar. 1, 2017, states that scientific studies have shown CBD to be useful in the field of medicine, including the following: to treat epilepsy, as a neuroprotective compound to preserve brain matter in stroke and traumatic brain injury, to treat post-traumatic stress disorder (PTSD), and as an anti-tumor agent that has been shown to be effective in vitro and in mouse studies in inhibiting malignant cell growth of multiple cancers.

Over the centuries, the scientific community has been divided over the taxonomical definition of species of the *Cannabis* genus. Colloquially, two separate species, *Cannabis sativa* and *Cannabis indicia*, are used as a convenient way to differentiate *Cannabis* plant varieties with higher CBD from *Cannabis* varieties with higher THC content. However, as reported in *Cannabis* and Cannabinol Research (Hazekamp, et al.; *Cannabis* and Cannabinoid Research 2016, 1.1) current scientific research has shown that *Cannabis* is monotypic and consists of only a single species *Cannabis sativa L*. Within this species there are two subspecies. One subspecies is a non-drug, fiber-type cannabis having a higher CBD content. It was originally grown on an industrial scale for fiber, oil, and animal feedstuff, and, thus, it is often referred to as "hemp" or "industrial hemp." The oil derived from this subspecies will be herein referred to as "hemp oil." The other subspecies is the drug-type cannabis that has a higher THC content, which is often referred to as "marijuana." Oil derived from this subspecies will be herein referred to as "hash oil." The oil derived from any of the species or subspecies of the *Cannabis* genus will be referred to herein as "*Cannabis* oil."

Plant matter of the *Cannabis* genus is often vaporized and inhaled through smoking. Typically, plant matter filler is wrapped in a thin exterior wrapper and rolled into a slim, elongated plant-filled smokable cylindrical roll (similar to a tobacco-filled cigarette), which may be referred to as a joint, blunt, cigarette, spliff, or other terms, but is herein termed a "joint/blunt." The wrapper may be formed of tobacco, hemp, wood pulp, and the like and may be thicker (burning more slowly) or thinner (burning more quickly). The plant matter used as a filler in the smokable cylindrical rolled joint/blunt may be from the *Cannabis* plant or a mixture of *Cannabis* matter and matter from the tobacco plant. Other methods of vaporization include pipes and water pipes designed for burning the plant product.

Though inhalation is an effective means of intake for CBD, and though CBD is known to alleviate various medical conditions, it has been difficult for medical providers to prescribe a dosage. This is partially due to the variation in the amount of CBD in the various *Cannabis* cultivated varieties. Although a patient may receive a higher dosage if a varietal with a higher CBD content is chosen than if a varietal with a lower CBD content is chosen, it still remains that to achieve the prescribed or desired CBD intake the user may have to smoke more of the product than is wanted. Thus, there is a need for a product with a consistent and regulated amount of CBD and for a process which reliably produces this product in which the level of CBD can be controlled. This would allow the medical provider to prescribe a dosage of CBD and to allow the user to be informed of the dosage of CBD. Also, it would be desirable to provide a higher dosage of CBD than is available in the natural plant product.

Another problem related to the above example has been in attempting to add oil to marijuana products, because, when attempted, the results have been inconsistent and have produced a less than desirable product. For example, to increase the THC content of marijuana before smoking, some users squirt thick hash oil onto marijuana buds, which are then shredded, placed in a wrapper, and rolled to form a smokable cylindrical rolled joint/blunt. The oil remains on the outside of the buds in an unequal distribution. This results in an inconsistent burn, often requiring the joint/blunt to be relit during smoking. Thus, there is a need for a process which dependably produces an oil-infused product that has a consistent oil dispersion to yield a consistent burn.

In addition to the above example of the combination of plant matter with *Cannabis* oil, it would be desirable to efficiently control the ratios of other oils with other plant matter to provide health and therapeutic benefits. Additionally, in other instances there is a need to increase the proportion of the weight of the oil per the weight of the plant matter, and no conventional method allows this increase.

Accordingly, there is a need for a dependable, quality oil-infused plant product in which the potency of the infused oil can be controlled, in which the potency and ratio can be increased beyond what is currently available, and in which the oil is distributed consistently. In addition, there is a need for a process that provides this oil-infused plant product while minimizing degradation of the plant matter.

BRIEF SUMMARY OF THE INVENTION

The present invention is directed to an oil-infused plant product and method of processing. In overview, the method includes the steps of placing dried botanical matter coated with a mixture of alcohol and oil (which in some aspects includes one or more additives) into a pressurizable container, pressurizing and heating the pressurizable container, allowing the botanical matter with the oil/alcohol mixture to remain in the container for a development time period, removing the remains of the oil/alcohol mixture via a vacuum, and retrieving the oil-infused plant matter from the pressurizable container.

Any of a variety of oils and any of a variety of plant matter may be used in the process. Any of a variety of additives may be added to the oil/alcohol mixture.

The disclosed process provides a quality oil-infused plant product in which the potency and ratio of the infused oil can be controlled, in which the potency of the oil can be increased beyond what is currently available, in which the ratio of oil to botanical matter can be increased beyond what is currently available, and in which the oil is distributed consistently while minimizing degradation of the plant matter.

In one aspect of the invention, the botanical matter may be processed plant matter.

In another aspect of the invention, the processed plant matter may be a blunt wrapper (also called a "rolling paper") that may be formed substantially of hemp, tobacco, other types of plant matter, or plant matter in combination with synthetic materials and in which the processed plant matter has been processed to form a thin sheet suitable for containing a product and for rolling a slim, elongated smokable cylindrical rolled joint/blunt containing the product.

In another aspect of the invention, the botanical matter may be a minimally processed plant matter.

In an additional aspect of the invention, the botanical matter may be a natural plant matter.

In a further aspect of the invention, the botanical matter may be a plant product suitable for brewing.

In an additional aspect of the invention, the botanical matter may be a smokable plant product.

In another aspect of the invention, the botanical matter may be dried herbs.

In a further aspect of the invention, the botanical matter may be hemp.

In another aspect of the invention, the botanical matter may be coffee beans.

In an additional aspect of the invention, the botanical matter may be dried *Cannabis* plant matter.

In a further aspect of the invention, the botanical matter may be tobacco.

In another aspect of the invention, the botanical matter may be goto kola, also known as *Centella asiatica*.

In a further aspect of the invention, the oil used for infusion is a *Cannabis* oil.

In an additional aspect of the invention, the infusing oil may be hemp oil.

In a further aspect of the invention, the infusing oil may be high-CBD hemp oil.

In another aspect of the invention, the infusing oil may be a hash oil.

In a further aspect of the invention, the infusing oil may be high-THC hash oil.

In another aspect of the invention, the infusing oil may be a combination of hash oil and hemp oil.

In another aspect of the invention, the infusing oil may be coconut oil.

In another aspect of the invention, the infusing oil may be black seed oil.

In another aspect of the invention, the infusing oil may be an essential oil.

In another aspect of the invention, one or more additives are added to the oil and alcohol mixture.

An object of the present invention is to provide a process for producing an oil-infused plant product that introduces the oil into the dry plant matter instead of merely coating the surface of the dry matter with oil.

An additional object is to infuse an oil into any of a variety of dry botanical plant matter.

These and other objects, features, and advantages of the present invention will become more readily apparent from the attached drawings and from the detailed description of the preferred embodiments which follow.

BRIEF DESCRIPTION OF THE SEVERAL VIEWS OF THE DRAWINGS

The preferred embodiments of the invention will hereinafter be described in conjunction with the appended drawings, provided to illustrate and not to limit the invention, where like designations denote like elements.

Like reference numerals refer to like parts throughout the several views of the drawings.

DETAILED DESCRIPTION OF THE INVENTION

Shown throughout the figures, the present invention is directed toward an oil-infused plant product 50 and toward a method of processing prepared (dried and/or cured and the like) botanical matter 20 with a mixture 60 of alcohol 30 and oil 40 (and, in some aspects, one or more additives) to produce, using heat and pressure, the inventive oil-infused plant product 50.

Figure 1:
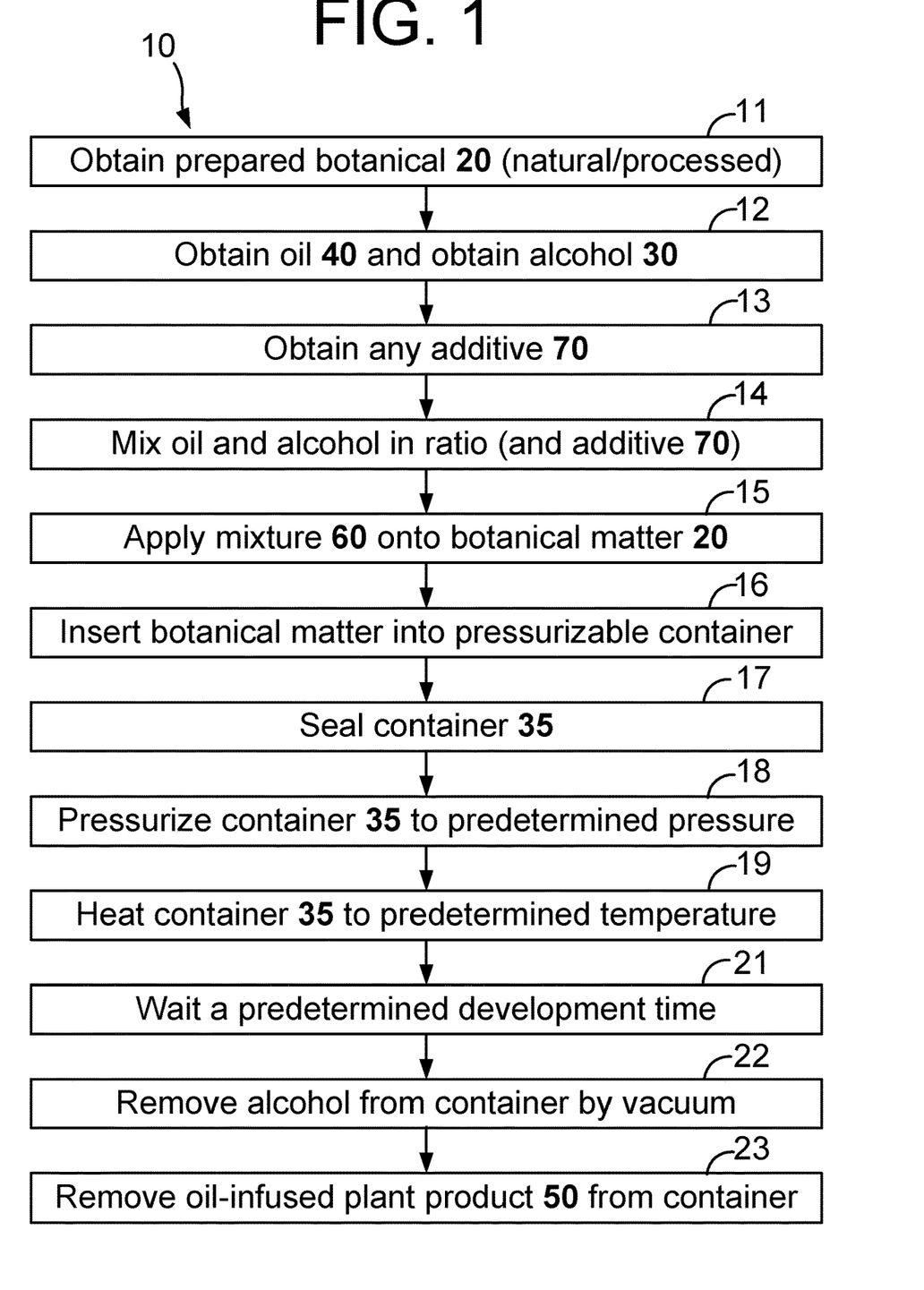
FIG. 1 is a flowchart showing an embodiment of the method of processing the botanical material to create the oil-infused plant product of the present invention.

Referring now to FIG. 1, the producer who is to produce the oil-infused plant matter product 50 first obtains 11 the type of prepared botanical matter 20 to be infused, obtains 12 the type of oil 40 that is desired, obtains 12 the type of alcohol 30 to be used, and obtains 13 any additive 70 to be included in the mixture.

The oil 40 used may be any of a variety of oils or lipids that are suitable for human consumption, for smoking, or for application to human skin. The oil 40 may be any oil of animal, vegetable, or petrochemical origin. The oil 40 is substantially a nonpolar chemical substance that is hydrophobic and lipophilic but may include a low proportion (less than 10%) of non-oil components, which may be naturally occurring with the hydrophobic lipids or may be additives to it. The non-oil components may be, for example, proteins, waxes, alkaloids, or the like. Suitable oils 40 include *Cannabis* oil, olive oil, sunflower seed oil, butter, corn oil, essential oil (such as lavender, lemon, orange, Bergamot, frankincense, etc.), coconut oil, almond oil, black seed oil, grapeseed oil, jojoba oil, shea butter, apricot kernel oil, argan oil, castor oil, evening primrose oil, marula oil, neem oil, palm oil, rosehip oil, pomegranate oil, rice bran oil, safflower oil, tamanu oil, avocado oil, and other nontoxic oils.

In one aspect of the invention, the oil 40 comprises a *Cannabis* oil. In this aspect, the oil 40 is *Cannabis* oil extracted from plants of the genus *Cannabis*, which includes both the hemp plant cultivated varieties (higher CBD and little or no THC) and the marijuana plant cultivated varieties (higher THC than the hemp cultivated varieties). The *Cannabis* oil may be any oil extracted from plants of the genus *Cannabis*, including hemp oil extracted from the hemp plant, hash oil extracted from the marijuana plant, and hemp and hash oil mixtures. The *Cannabis* oil may be extracted in any conventional manner, such as those methods using a solvent, which may be, for example, butane, ethanol, chloroform, ethanol, isopropanol, and the like. The *Cannabis* oil may be extracted from any part of the plants of the *Cannabis* genus, which is preferably dried before the oil is extracted. Preferably the *Cannabis* oil selected for use contains minimal or no residual traces of any solvent used in the extraction process.

The botanical matter 20 that is used in the processing method is prepared for use, which includes drying or curing or the like, before beginning the inventive process. For example, the drying and curing may have been performed by carrying out any of the variety of known drying and curing procedures. The drying may be by air drying or, more preferably, by using a dehydrator or forced-air dryer. The botanical matter 20 may be a processed plant matter, such as a blunt wrapper, or may be a natural or minimally processed plant matter, such as, for example, *Cannabis* plant matter, dried smokable herbs, or dried herbs suitable for brewing including coffee and tea. The botanical matter 20 may be used whole or in particulate form. For example, coffee beans or ground coffee may be used.

The botanical matter 20 used may be derived from any portion of the plant (stem, roots, leaves, buds, flower portions, bark, rhizomes, fruit, etc.) with different plant portions utilized depending on the particular plant variety that has been selected for the infusion process. The botanical matter 20 may be the whole plant (such as *Centella asiatica*), may be leaves (such as tea leaves, hemp leaves, or *Vitex negundo* leaves), may be buds (such as *Cannabis* buds), may be bark (such as the bark of cinnamon trees of the genus *Cinnamomum*), may be seeds (such as coffee or celery), may be fruits (such as *xanthocarpum, Emblica*, or *Terminalia*), may be rhizomes (such as *Curcuma longa* or *Cyperus rotundus*), may be gum or gum resins (such as *Boswellia serrata* or *Commiphora mukul*) or may be roots (such as the dried root of the celery plant (*Apium graveolens*). As an example, the botanical matter may be, but is not limited to, any of the following: tea leaves, coffee beans (ground or preferably whole), yarrow flower (*Achillea millefolium*), *Salvia* species (including sages, *Salvia apiana*, and *Salvia divinorum*), Lamiaceae species (including peppermint and spearmint), *Leonotis* species (including wild dagga and klip dagga), plants of the Papaveraceae family (including celandine poppy and California poppy), blue lotus (*Nymphaea caerulea*), kratom, tobacco, herbal non-tobacco, mugwort, coltsfoot leaf, *Heimia salicifolia*, St. John's wort, *Melissa officinalis*, skullcap (*Scutellaria laterifolia*), yerba lenna yesca, *Capillaris Herba, Calea zacatechichi, Leonurus sibericus*, damiana, kava, *Avena sativa*, valarian, kanna, *Lactuca virosa*, clove, myrrh, willow, *Cornus* (dogwood including red osier), pipsissewa (*Chimaphila umbellata*), pyrola, kinnikinnik, *Arctostaphylos uva-ursi*, camomile, manzanita, *Arctostaphylos* species, madrone, *Arbutus menziesii, Rubus* species (raspberry, blackberry, etc.), scotch broom (*Cytisus scoparius*), *Cannabis* species (including marijuana and hemp), calamus, *Verbascum* species (mullein), *Cinnamomum* species, *Elettatia cardamomum*, plants of the *Aquilaria* genus, *Crocus sativus, Santalum album, Withania somnifera, Mucuna pruriens, Celastrus paniculatus, Emblica officinalis, Terminalia chebula, Terminalia bellerica, Solanum xanthocarpum, Glycyrrhiza glabra* (licorice), *Ocimum sanctum*, plants of the Zingiberaceae family (including *Curcuma longa* (turmeric) and *Zingiber officinale* (ginger), a'hai, celery plant (*Apium graveolens*), *Commiphora mukul, Boswellia serrata, Vitex negundo, Bacopa monnieri, Cyperus rotundus, Myristica fragrans, Valeriana wallichii, Nardostachys jatamansi, Mimosa hostilis, Acacia confusa*, Passifloraceae species, *Echinacea purpurea*, milk thistle (*Silybum marianum*), *Angelica* species (including *Angelica archangelica*), catnip plants (*Nepeta cataria*), lavender (including *Lavandula angustifolia*), *Taraxacum* species (including dandelion), linden tree flowers, lemon verbena (*Aloysia citrodora*), and gotu kola (*Centella asiatica*).

The alcohol 30 that is used as a solvent in the process 10 may be any type of primary, secondary, or tertiary alcohol, including, but not limited to ethanol (including beer, wine, and distilled liquor containing varying amounts of ethanol), isopropyl alcohol, propylene glycol (which is preferred), and other nontoxic alcohols. The alcohol 30 may optionally be ethanol derived from the biomass of lignocellulosic crops, which are pretreated to loosen the lignocellulosic structure and to facilitate enzymatic hydrolysis of polysaccharides prior to ethanol fermentation, such as the method using dilute combined steam (140-180 C) and dilute-acid prehydrolysis (0.0-2.0%) described by Kuglarz et al. in Volume 163, July 2014, pages 236-243 of Bioresource Technology, which is incorporated by reference. Optionally, the alcohol 30 may be ethanol derived from hemp; such a derivation process may include fermenting the stalks and using gasification, acid hydrolysis and enzymes.

After obtaining 11, 12, 13 (FIG. 1) the botanical matter 20, oil 40, alcohol 30, and any additive 70, the producer creates 14 a mixture 60 of the oil 40 and alcohol 30 using a specific ratio. The specific ratio of alcohol 30 to oil 40 is between 1 to 12 and 12 to 1 and is preferably between 4 to 6 and 6 to 4. By increasing the percentage of oil 40 in the oil/alcohol mixture, the potency of the infused product can be increased. For example, an alcohol to oil ratio of 4 to 6 provides a higher potency final oil-infused plant product than an alcohol to oil ratio of 6 to 4.

In addition to the oil 40 and alcohol 30, any additive 70 to be included in the infused plant product can be added and blended into the oil and alcohol as a part of the oil/alcohol mixture 60. In one aspect, the additive 70 is added to the oil 40 before the oil 40 and alcohol 30 are mixed. In another aspect, the additive 70 is added to the alcohol 30 after the oil 40 and alcohol 30 are mixed. In another aspect, the additive 70 is added to the alcohol 30 before the oil 40 and alcohol 30 are mixed. In one aspect of the invention, the mixing of the oil 40 and alcohol 30 and any additive 70 is performed mechanically or through robotic means. In another aspect, the mixing may be done manually.

After mixing, the oil/alcohol mixture 60 is then applied to the botanical matter 20.

In one aspect of the invention, the oil/alcohol mixture 60 may be poured onto the botanical matter 20. This may be done manually or through use of mechanical or robotic means.

In another aspect, the oil/alcohol mixture 60 is introduced into a sprayer 65 that is functional to spray a coating of the oil/alcohol mixture 60 onto the botanical matter 20. Preferably the sprayer 65 distributes the oil/alcohol mixture 60 uniformly in a light mist. The sprayer 65 may be a compressed gas sprayer, a high-volume low pressure (HVLP) sprayer, an airless paint sprayer, an electrostatic sprayer, a rotary disk sprayer, or other sprayer as is known in the art. The HVLP sprayer may utilize a turbine that delivers a high volume of air at a very low pressure, such as about five pounds per square inch (psi) or may be a conversion HVLP that utilizes the air from a compressor at about twenty-five psi. The sprayer 65 typically includes a tank to receive the oil/alcohol mixture 60 and a spray head or nozzle. Optionally the sprayer 65 may include an agitator to stir the mixture to keep it in a homogeneous state. Preferably the sprayer 65 has a pressure adjustment.

In a preferred aspect, the botanical matter 20 is disbursed to facilitate the application of the oil/alcohol spray from the sprayer 65, such as being spread to form a single layer. The botanical matter 20 is then sprayed with the oil/alcohol mixture 60. The spray from the sprayer is directed either manually or by mechanical means (such as by a robotic or mechanical arm) in such as manner as to distribute the oil/alcohol mixture 60 onto the botanical matter 20 in a generally uniform manner.

By applying the spray generally uniformly over the botanical matter 20, a known weight of oil 40 can be applied to a known weight of botanical matter 20, thus allowing the producer to produce an oil-infused product 50 with a consistent, known, and controlled amount of oil per product weight. The ratio of oil to botanical matter may be in the range of from 0.1 to 1 gram of oil to 1 gram of dried botanical matter. In one aspect of the invention, the ratio of oil to botanical matter is 0.25 gram of oil (which is mixed with the alcohol carrier in the specific ratio) to one gram of botanical matter. In another aspect, the ratio of oil to botanical matter is 0.5 grams of oil (which is mixed with the alcohol carrier in the specific ratio) to one gram of botanical matter. In an example, if a particular variety of high-CBD hemp buds are to be used as the botanical matter and if hemp oil is to be used as the oil 40, an average CBD content for 1 gram of the particular variety of high-CBD hemp can be known or determined, and the CBD content for the specific weight of oil applied to one gram of the high-CBD hemp can be known or determined. Therefore, the total CBD content can be known or determined by the producer, which can be provided to medical personnel for accurate dosing. Additionally, the amount of CBD in a particular weight of product can be increased by increasing the weight of oil applied to the botanical matter. Thus, a person who needs a higher dosage of CBD will not need to smoke more product but can instead smoke a product with a higher ratio of oil to dried botanical matter. Similarly, the amount of additive 70 is a known amount.

After applying 15 the oil/alcohol mixture 60 onto the botanical matter 20, the oil/alcohol-covered botanical matter, which is now more pliable and holds together better, is placed 16 into the pressurizable container 35. This oil-treated botanical matter 20 may be placed directly into the container 35 or it may be placed on racks, into mesh baskets, or into other interior organizing apparatuses, which are then placed into the container 35. Whether the botanical matter 20 is placed into the container 35 with an interior organizing apparatus and the type of interior organizing apparatus to be used is based primarily on the type and particle size of botanical matter 20 that has been chosen by the producer to be infused.

In one aspect of the invention, the pressurizable container 35 is a container suitable for being pressurized at least up to 55 psi and preferably up to 80 psi. In another aspect, the pressurizable container 35 can be pressurized to a higher pressure.

The pressurizable container 35 has an interior large enough to receive the amount of botanical matter 20 being processed and can be closed and/or sealed, such as with a lid or door. An air compressor or air pump may be attached to an inlet to increase the pressure 18 within the container 35 (after closure) to the specific pressure.

After sealing 17 the pressurizable container, it is pressurized 18 to a specific level of pressure. The specific pressure is in the range of 1 to 1000 psi. In one aspect the specific pressure is in the range of 20 to 100 psi. In another aspect, the specific pressure is in the range between 60 to 80 psi. Additionally, the container 35 (containing the oil/alcohol-covered botanical matter) is heated 19 to a specific temperature in the range of 90 to 190 degrees Fahrenheit, and preferably in the range of 125 to 175 degrees Fahrenheit. The heat may be generated by an integrated energy source or an external energy source. The energy source provides thermal energy in a form such as by radiant heat, heated air or other fluid, electromagnetic heat induction, electric current, and any combination thereof.

The oil/alcohol-covered botanical matter remains in the sealed, heated, pressurized container 35 for a development period of time 17 during which the infusing oil 40 penetrates deeply into the tissue of the botanical plant matter 20. Due to the pre-treatment of the botanical matter with the oil, there is minimal degradation of the botanical matter during this processing time.

The development time is in the range of two hours to twenty days. In one aspect, the development time is in the range from three to thirty hours. In one preferred aspect, the development time is from five to twenty-four hours. The development time may be based on factors such as the type of botanical matter 20, the specific temperature deemed optimum for the particular type of botanical matter 20, the pressure selected as optimum for the particular type of botanical matter 20, the type of alcohol 30, the type of oil 40, the type and amount of any additive 70, the ratio of oil to alcohol, the ratio of the weight oil/alcohol mixture 60 to the weight of the botanical matter 20, and the like.

After waiting the specific development time 21, any residual oil/alcohol mixture (since the oil is absorbed, the residue is substantially alcohol) is removed 22 from the container 35 by a via a vacuum pump.

The newly created oil-infused plant product 50 is then removed 23 from the container 35 and is ready for packaging for sale or for use.

If the producer desires to create an oil-infused plant product 50 with one or more additives 70, the additive is added to, and incorporated into, the oil/alcohol mixture 60 as the mixture 60 is created. This allows the additive 70 to be mixed with the oil 40 and alcohol 30 and to be applied 15 onto the botanical matter 20. The oil/alcohol mixture 60 (including the additive 70) is then applied to the botanical matter 20. The additive 70 is then absorbed into the botanical matter 20 with the oil, as both penetrate the flesh of the botanical matter, which occurs substantially during pressurization.

The additive 70 may be any of a variety of ingredients that augment or complement the oil 40, the alcohol 30, the oil/alcohol mixture 60, and/or the botanical matter 20 and/or that augments or complements the health benefits of the oil-infused plant product 50. In addition to improving therapeutic benefits, the additive 70 may improve the look or presentation, the taste or flavor, the smell, the mouth feel, the ease of application, the ability to smoke a smokable end product, or other characteristic of the oil/alcohol mixture 60. The additive 70 may be all natural, all artificial, or a blend of natural and artificial components. In one aspect of the invention, the additive 70 is a flavor enhancing material, such as a fruit flavoring (apple, strawberry, peach, grape, lemon, etc.), a nut flavoring, an herbal scent and/or flavoring (mint, lavender, rosemary, eucalyptus, etc.), or the like. In another aspect, the additive 70 may be a vitamin or vitamin mixture. In an additional aspect the additive 70 may be a nutraceutical or other health-benefiting additive. In a further aspect, the additive may be terpenes, cannabinoids, or entourage chemicals from the *Cannabis* plant. In yet another aspect, the additive 70 may be nicotine, which may provide benefits to the user including aiding in smoking cessation, improvement in brain function, combating depression, increasing attention, and preventing Parkinson's disease. In an example, the oil 40 used is MCT coconut oil, the botanical matter 20 used is tea, and the additive 70 used is a vitamin complex. In another example, the oil 40 used is avocado oil, the botanical matter 20 used is coffee, and the additive 70 used is nicotine.

Figure 2:
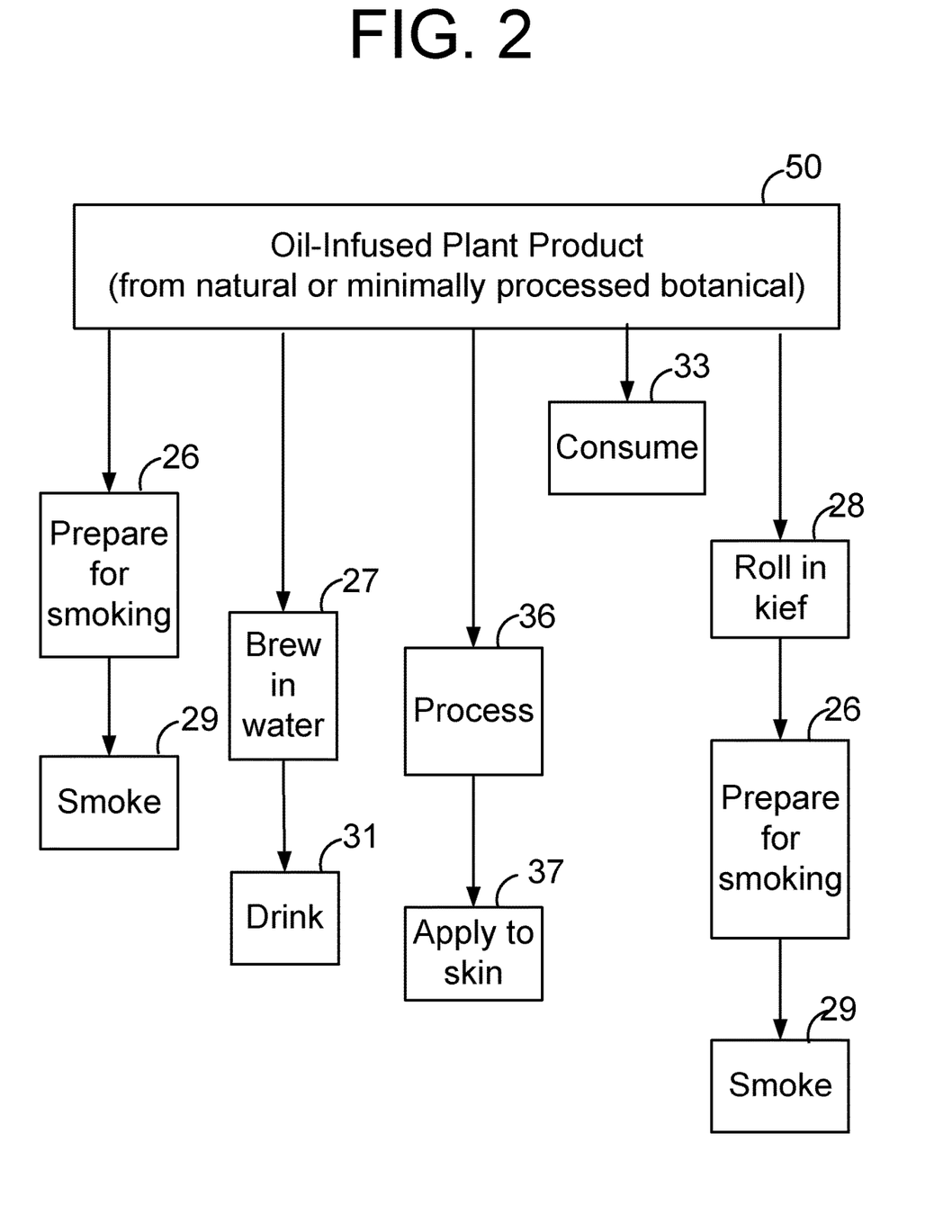
FIG. 2 is a flowchart showing potential exemplary uses of the oil-infused plant product from natural or minimally processed botanical matter of the present invention.
Figure 3:
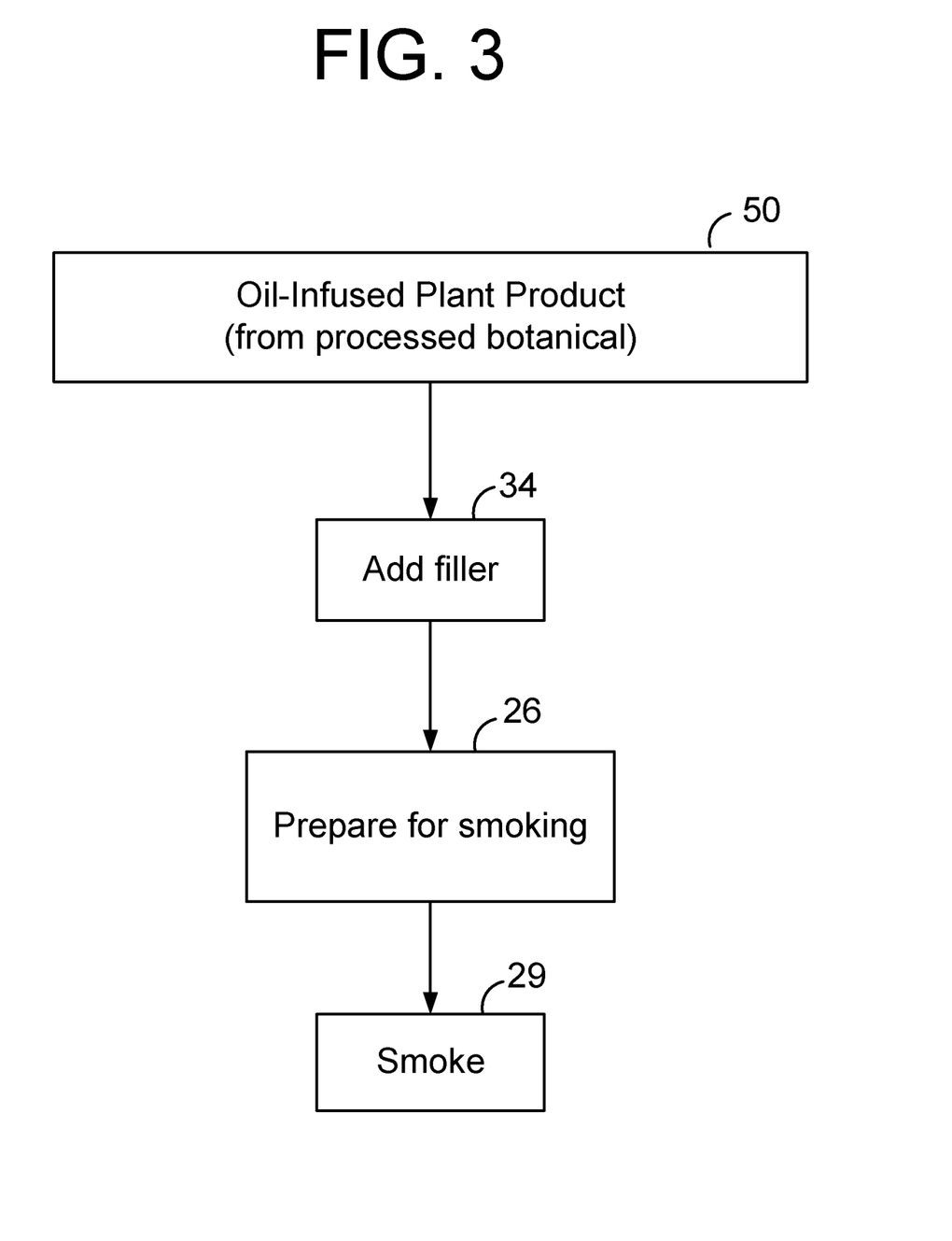
FIG. 3 is a flowchart showing potential exemplary uses of the oil-infused plant product from processed botanical matter of the present invention.

FIGS. 2 and 3 illustrate exemplary uses for the oil-infused plant product 50. The uses of the oil-infused plant product 50 will vary based on factors such as the type and varietal of the plant used for the initial botanical matter 20, whether the botanical matter 20 was processed or natural/minimally processed before infusing, and the type of oil 40 used in the infusion process. The uses of the oil-infused plant product 50 may be influenced by the additive 70 that has been infused along with the oil 40.

FIG. 2 illustrates exemplary uses for an oil-infused plant product 50 that is produced from a natural or minimally processed plant matter 20. In a first exemplary use, the oil-infused plant product 50 is prepared 26 for smoking. The oil-infused plant product 50 is prepared for smoking by being formed into a joint/blunt using paper or cones and smoked 29. In another aspect, the oil-infused plant product 50 may be placed into a pipe for smoking 29. In an example, if the oil 40 comprises hash oil and the botanical matter 20 comprises cannabis material, the infused plant material 50 will be hash oil-infused *Cannabis* that may be prepared for smoking 26 such as formed into a joint/blunt or optionally smoked in a smoking pipe or water pipe.

In a second exemplary use shown in FIG. 2, the oil-infused plant product 50 can be brewed or steeped 27 in water to make tea or coffee, which a user can subsequently drink 31. In an example, using a hemp oil for the oil 40 and the leaves of the gotu kola plant as the botanical matter 20, the resulting hemp oil-infused gotu kola product 50, which will not be psychoactive, can be used as a filler in the preparation for smoking 26, such as forming a joint/blunt (as in the first exemplary use) or can be steeped 27 in water for drinking 31 as a tea (as in the second exemplary use). In this example, if CBD hemp oil (or high-CBD oil) is used as the oil 40, the ratio of *Cannabis* oil to alcohol 30 can be varied to control the potency of the CBD. The potency may range from 50 mg/gram to 3.5 gram/gram. The regulation of the dosage through use of this infusion process 10 allows for a consistency of therapeutic effect that is not currently available. Additionally, a larger amount of CBD can be introduced into a smaller amount of plant matter compared to conventional processing means, thus a larger dosage of CBD can be administered in a shorter smoking session because the potency of the product is higher when produced in this manner. In a further example of a brewable oil-infused plant product 50, the botanical matter 20 may be tea and the oil 40 may be lavender essential oil. This example produces a flavored tea with the benefits of the essential oil.

FIG. 2 also shows the third exemplary use of the oil-infused plant product 50, which is for application 37 to the skin. The oil-infused plant product 50 is processed 36 and packaged for sale and use. In one aspect of the invention, a quantity of the oil-infused plant product 50 is applied to the skin and secured in place to form a type of poultice. In another aspect, a granulated oil-infused plant product 50 is applied to the skin by hand, brush, washcloth, or the like. In this aspect, the oil-infused plant product 50 is used as a scrub on the skin. In an example of the oil-infused plant product 50 used as a scrub, the botanical matter 20 may be ground coffee beans, the oil 40 may be MCT coconut oil, and the additives 70 may be terpenes and nicotine. This combination may provide benefits to the skin beyond merely removing dead skin, such as smoothing the skin, reducing blemishes, and refreshing and repairing the skin.

A fourth exemplary use of the oil-infused plant product 50 is also shown in FIG. 2. In this exemplary use, the oil-infused plant product 50 is consumed 33 by the user. An example of botanical matter 20 that can be infused and then eaten 33 is hemp seed (whole or ground) that is infused with black seed oil. Health-enhancing additives 70 may suitably be added to the oil-infused plant product 50, such as vitamins, minerals, ornus gold, monoatomic gold, and the like.

Also shown in FIG. 2 is the fifth exemplary use of the oil-infused plant product 50 produced from a natural or minimally processed plant matter 20. In this exemplary use, the oil-infused plant product 50 can be removed from the container 35 and rolled 28 in kief. A blunt/joint can then be formed 26 from the kief-covered, oil-infused botanical filler. For example, if marijuana buds are used as the botanical matter 20 and hash oil is used for the oil 40, the *Cannabis* oil-infused marijuana buds 50 will have a sticky exterior, so when rolled 28 in kief, the kief will adhere to the buds. The oil-infused buds with adhered kief can then be used as a filler to be placed in a rolling paper, rolled, and sealed to form 26 an elongated cylindrical blunt/joint, which can be smoked 29. These *Cannabis* oil-infused marijuana buds with adhered kief provide a better and more consistent burn compared to currently available products where an oil is merely applied to the exterior of the buds. Other methods of smoking the oil-infused, and optionally kief-covered, plant product 50 include using a smoking pipe or a water pipe.

FIG. 3 illustrates an exemplary use for an oil-infused plant product 50 that is produced from a processed plant matter 20. In this exemplary use case, the initial botanical matter 20 used may be a wrapper produced solely from hemp, produced primarily from hemp, or produced from one or more other natural products, such as flax, sisal, rice straw, and esparto. Less preferably, a wrapper may be formed from all or partially manmade products. The wrapper may also incorporate one or more supplemental components, which may include chemical components that regulate combustion (such as sodium potassium tartrate, sodium citrate, potassium citrate), that influence the permeability (such as calcium carbonate), or that influence the color (such as magnesium carbonate or titanium oxide). Any and all of these wrappers of various compositions are generically referred to herein as a "hemp wrapper."

The hemp wrapper is formed in a conventional manner, such as, in a non-limiting example, by pulverizing the hemp plant material with liquid present to form a paste, spreading the paste into a thin sheet, and drying the sheet. Or the hemp wrapper may be formed in any other conventional manner.

After obtaining 11 the processed botanical items 20, for example the dried hemp wrappers, they are spread out, such as in a single layer. The mixture of oil and alcohol is then sprayed onto the hemp wrapper 20, as described above in the spraying of the natural botanical matter 20. This creates an oil/alcohol-coated hemp wrapper that is then placed 16 into the pressurizable container 35. The oil/alcohol-coated hemp wrapper may be placed directly into the container 35 or may be placed on a rack-type interior organizing apparatus inside the container 35. For example, stacks of from twenty to thirty wrappers may be introduced into the container 35. After pressurization and heating 18, 19, after the passage of the development time 21, and after the removal 22 of the alcohol, as described in FIG. 1, the oil-infused wrappers 50 are removed 23 and are ready for packaging or use.

To use, a filler material is added 34 to the oil-infused wrapper 50, the wrapper 50 is rolled around the filler and is generally sealed with an adhesive to form a joint/blunt in preparation 26 for smoking 29. The filler may be any material that the user desires to smoke, including tobacco, any of the other plants listed above as suitable for use as botanical matter 20, and any of the types of oil-infused plant matter 50 provided by the instant invention.

In all the smokable forms of the oil-infused plant matter 50, the inventive process produces a product with a good taste that has consistent oil distribution that is not merely on the exterior of the product, so that it burns dependably and does not have to be relit.

The inventive process provides a means to control the dose of therapeutic agents, such as CBD, in the oil-infused plant matter 50 output from the process and to increase the dose of therapeutic agents above the currently available dosages.

The invention illustratively disclosed herein suitably may be practiced in the absence of any element which is not specifically disclosed herein.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A method for making an oil-infused plant-based product comprising:
    mixing an alcohol and an oil to create an oil/alcohol mixture having a ratio of the alcohol to the oil between 2.5 to 7.5 and 7.5 to 2.5, wherein said mixing step further comprising the step of adding an additive to said oil/alcohol mixture;
    applying said oil/alcohol mixture onto dried botanical matter to create an oil/alcohol coated botanical matter;
    placing said oil/alcohol coated botanical matter into a pressurizable container;
    pressurizing said pressurizable container to a pressure level between 65 and 75 psi;
    heating said pressurizable container to a temperature in the range of 125 to 175 degrees Fahrenheit;
    leaving said dried botanical matter coated with said oil/alcohol mixture in said pressurizable container at said pressure and said temperature for a development time period in a range of 3 hours to 25 hours to create an oil-infused botanical product;
    removing any residual portion of said oil/alcohol mixture from said oil-infused botanical product; and
    removing said oil-infused botanical product from said pressurizable container.

2. The method for making a plant-based product, as recited in claim 1, wherein said alcohol is an organic solvent comprising one or more of the following group: propylene glycol and ethanol.

3. The method for making a plant-based product, as recited in claim 1, wherein said oil comprises one or more of the following group: hemp oil, hash oil, olive oil, sunflower oil, butter, corn oil, essential oil, coconut oil, almond oil, black seed oil, grapeseed oil, jojoba oil, shea butter, apricot kernel oil, argan oil, castor oil, evening primrose oil, manila oil, neem oil, palm oil, rosehip oil, pomegranate oil, rice bran oil, safflower oil, tamanu oil, and avocado oil.

4. The method for making a plant-based product, as recited in claim 1, wherein said dried botanical matter comprises a processed wrapper formed of natural materials.

5. The method for making a plant-based product, as recited in claim 1, wherein said dried botanical matter comprises one of the following group: tobacco, a *Cannabis* species, coffee beans, tea, and gotu kola.

6. The method for making a plant-based product, as recited in claim 1, wherein said dried botanical matter consists of one of the following group: tea leaves, coffee beans, gotu kola, *Achillea millefolium*, *Salvia* species, Lamiaceae species, *Leonotis* species, plants of the Papaveraceae family, *Nymphaea caerulea*, kratom, tobacco, herbal non-tobacco, mugwort, coltsfoot leaf, *Heimia salicifolia*, St. John's wort, *Melissa officinalis*, *Scutellaria laterifolia*, yerba lenna yesca, *Capillaris herba*, *Calea zacatechichi*, *Leonurus sibericus*, damiana, kava, *Avena sativa*, valarian, kanna, *Lactuca virosa*, karma, clove, myrrh, willow, *Cornus* species, *Chimaphila umbellata*, pyrola, kinnikinnik, *Arctostaphylos uva-ursi*, camomile, manzanita, *Arctostaphylos* species, madrone, *Arbutus menziesii*, raspberry, blackberry, *Rubus* species, *Cytisus scoparius*, *Cannabis* species including marijuana and hemp, calamus, *Verbascum* species (mullein), *Cinnamomum* species, *Elettatia cardamomum*, plants of the *Aquilaria* genus, *Crocus sativus*, *Santa/um album*, *Withania somnifera*, *Mucuna pruriens*, *Celastrus paniculatus*, *Emblica officinalis*, *Terminalia chebula*, *Terminalia*

*bellerica, Solanum xanthocarpum, Glycyrrhiza glabra, Ocimum sanctum*, plants of the Zingiberaceae family, a'hai, *Apium graveolens, Commiphora mukul, Bowellia serrata, Vitex negundo, Bacopa monnieri, Cyperus rotundus, Myristica fragrans, Valeriana wallichii, Nardostachys jatamansi, Mimosa hostilis, Acacia confusa, Passifloraceae species, Echinacea purpurea, Silybum marianum, Angelica species, Nepeta cataria, Lavandula angustifolia, Taraxacum* species, linden tree flowers, *Aloysia citrodora*, and *Centella asiatica*.

7. The method for making a plant-based product, as recited in claim 1, wherein said additive comprises one or more of the following group: a vitamin, a vitamin complex, a nutraceutical, flavoring enhancing material, nicotine, a terpene from the *Cannabis* plant, a cannabinoid from the *Cannabis* plant, and an entourage chemical from the *Cannabis* plant.

8. The method for making a plant-based product, as recited in claim 1, wherein the additive is a nicotine additive.

9. The method for making a plant-based product, as recited in claim 1, wherein applying said oil/alcohol mixture onto said dried botanical matter comprises spraying said oil/alcohol mixture in a uniform mist onto said dried botanical matter with a pressurized sprayer.

10. The method for making a plant-based product, as recited in claim 1, wherein:
   said oil comprises *Cannabis* oil;
   said alcohol is an organic solvent that comprises one or more of the following group: propylene glycol and ethanol;
   said dried botanical matter comprises one of the following group: tea leaves, coffee beans, gotu kola, *Achillea millefolium, Salvia* species, Lamiaceae species, *Leonotis* species, plants of the Papaveraceae family, *Nymphaea caerulea*, kratom, tobacco, herbal non-tobacco, mugwort, coltsfoot leaf, *Heimia salicifolia*, St. John's wort, *Melissa officinalis, Scutellaria laterifolia*, yerba lenna yesca, *Capillaris* Herba, *Calea zacatechichi, Leonurus sibericus*, damiana, kava, *Avena sativa*, valarian, kanna, *Lactuca virosa*, karma, clove, myrrh, willow, *Cornus* species, *Chimaphila umbellata*, pyrola, kinnikinnik, *Arctostaphylos uva-ursi*, camomile, manzanita, *Arctostaphylos* species, madrone, *Arbutus menziesii*, raspberry, blackberry, *Rubus* species, *Cytisus scoparius, Cannabis* species including marijuana and hemp, calamus, *Verbascum* species (mullein), *Cinnamomum* species, *Elettatia cardamomum*, plants of the *Aquilaria* genus, *Crocus sativus, Santalum album, Withania somnifera, Mucuna pruriens, Celastrus paniculatus, Emblica officinalis, Terminalia chebula, Terminalia bellerica, Solanum xanthocarpum, Glycyrrhiza glabra, Ocimum sanctum*, plants of the Zingiberaceae family, a'hai, *Apium graveolens, Commiphora mukul, Boswellia serrata, Vitex negundo, Bacopa monnieri, Cyperus rotundus, Myristica fragrans, Valeriana wallichii, Nardostachys jatamansi, Mimosa hostilis, Acacia confusa, Passifloraceae species, Echinacea purpurea, Silybum marianum, Angelica species, Nepeta cataria, Lavandula angustifolia, Taraxacum* species, linden tree flowers, *Aloysia citrodora*, and *Centella asiatica*.

11. The method for making a plant-based product, as recited in claim 10, wherein said additive comprises one or more of the following group: a vitamin, a vitamin complex, a nutraceutical, flavoring enhancing material, nicotine, a terpene from the *Cannabis* plant, a cannabinoid from the *Cannabis* plant, and an entourage chemical from the *Cannabis* plant.

12. The method for making a plant-based product, as recited in claim 10, wherein said additive comprises nicotine.

13. The method for making a plant-based product, as recited in claim 10, wherein said dried botanical matter consists of one of the following group: tobacco, a *Cannabis* species, tea, coffee beans, and gotu kola.

* * * * *